United States Patent
Hunt

(10) Patent No.: US 10,424,056 B2
(45) Date of Patent: *Sep. 24, 2019

(54) ACTIVE REAL-TIME CHARACTERIZATION SYSTEM FOR MONITORING ABSORPTION AND CURING RATES OF CHEMICAL SUBSTANCES

(71) Applicant: The Boeing Company, Chicago, IL (US)

(72) Inventor: Jeffrey H. Hunt, Thousand Oaks, CA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/901,972

(22) Filed: Feb. 22, 2018

(65) Prior Publication Data

US 2019/0259146 A1 Aug. 22, 2019

(51) Int. Cl.
*G06T 7/00* (2017.01)
*H04N 5/225* (2006.01)
(Continued)

(52) U.S. Cl.
CPC ......... *G06T 7/0004* (2013.01); *H04N 5/2256* (2013.01); *H04N 5/247* (2013.01);
(Continued)

(58) Field of Classification Search
CPC combination set(s) only.
See application file for complete search history.

(56) References Cited

U.S. PATENT DOCUMENTS 5,710,429 A * 1/1998 Alfano .................. G01N 21/49
250/330
5,973,778 A 10/1999 Hunt
(Continued)

FOREIGN PATENT DOCUMENTS

EP 2693187 B2 2/2014

OTHER PUBLICATIONS

Extended European Search Report dated May 31, 2019 in corresponding EP Application No. 19158905.0, 10 pgs.
(Continued)

*Primary Examiner* — Janese Duley
(74) *Attorney, Agent, or Firm* — Toler Law Group, PC

(57) ABSTRACT

An active real-time characterization system for monitoring the absorption and/or curing rate of a chemical substance applied to an outer surface of an article under test. Infrared and visible light sources controllably output a pulsed beam of coherent light directed at a particular area on the article under test where the chemical substance has been applied. A series of cameras, including a visible light camera, a visible light second harmonic generation camera, an infrared camera, an infrared second harmonic generation camera, a sum-frequency camera and a third-order camera are configured to receive return beams of light. A processor controls the pulse rate of the light sources and the first visible light source and processes the signals received from the cameras to determine when the chemical substance applied to the outer surface of the article under test has been absorbed or has cured.

20 Claims, 4 Drawing Sheets

(51) Int. Cl.
*H04N 5/247* (2006.01)
*H04N 5/33* (2006.01)

(52) U.S. Cl.
CPC ... *H04N 5/332* (2013.01); *G06T 2207/10048* (2013.01); *G06T 2207/10152* (2013.01)

(56) References Cited

U.S. PATENT DOCUMENTS

| | | |
|---|---|---|
| 6,781,686 B2 * | 8/2004 | Hunt .................. G06T 7/90 |
| 6,788,405 B2 | 9/2004 | Hunt |
| 6,795,175 B2 | 9/2004 | Hunt |
| 6,798,502 B2 | 9/2004 | Hunt |
| 6,819,844 B2 | 11/2004 | Hunt |
| 7,289,656 B2 | 10/2007 | Hunt |
| 7,304,305 B2 | 12/2007 | Hunt |
| 7,757,558 B2 | 7/2010 | Bossi et al. |
| 7,983,469 B2 | 7/2011 | Engelbart et al. |
| 8,664,583 B2 | 3/2014 | Hunt et al. |
| 8,789,837 B2 | 7/2014 | Chang et al. |
| 2013/0048841 A1 | 2/2013 | Hunt et al. |
| 2013/0050685 A1 | 2/2013 | Hunt et al. |
| 2016/0119557 A1 | 4/2016 | Hunt et al. |
| 2018/0275068 A1* | 9/2018 | Ozcan ................. G01N 1/34 |

OTHER PUBLICATIONS

Farsari M et al: "Holographic Characterization of Epoxy Resins At 351.1 NM" Optical Engineering, Soc. of Photo-Optical Instrumentation Engineers, Bellingham, vol. 37, No. 10, Oct. 1998, pp. 2754-2759.

K. B. Eisenthal: "Liquid Interfaces Probed by Second-Harmonic and Sum-Frequency Spectroscopy", Chemical Reviews, vol. 96, No. 4, Jan. 1996, pp. 1343-1360.

Mika Arai et al: "Curing Dynamics of Photopolymers Measured by Single-Shot Heterodyne Transient Grating Method" Analytical Sciences vol. 29, Apr. 2013, pp. 401-404.

Y. R. Shen: "Surface nonlinear optics [Invited]", A Journal of the Optical Society of America—B., vol. 28, No. 12, Dec. 2011, p. A56.

* cited by examiner

ACTIVE REAL-TIME CHARACTERIZATION SYSTEM FOR MONITORING ABSORPTION AND CURING RATES OF CHEMICAL SUBSTANCES

FIELD

This disclosure relates generally to an active real-time characterization system that monitors the absorption and curing rate of chemical substances applied to articles being manufactured.

BACKGROUND

During the manufacture of a parts for use in a larger assembly, it is common to apply a chemical substance such as a coating, paint, or primer to the outer surface thereof. The absorption rate and the curing rate of such chemical substances are extremely difficult to monitor to obtain accurate quantitative status information. Existing solutions used to obtain status information are based on historical data (from previous applications) combined with qualitative inspection and/or tactile interpretation and are thus unable to provide a desired level of accuracy.

Accordingly, there is a need for a monitoring system which addresses the drawbacks identified above.

SUMMARY

In a first aspect, an active real-time characterization system monitors the absorption and/or curing rate of a chemical substance applied to an outer surface of an article under test. An infrared light source controllably outputs a pulsed beam of coherent infrared light. The infrared light source is configured to direct the pulsed beam of coherent infrared light at a particular area on the article under test where the chemical substance has been applied. A first visible light source controllably outputs a first pulsed beam of coherent visible light. The first visible light source is configured to direct the first pulsed beam of coherent visible light at the same particular area on the article under test. A visible light camera and a visible light second harmonic generation camera are each configured to receive a first predetermined return beam of light from the particular area on the article under test. An infrared camera and an infrared second harmonic generation camera are each configured to receive a second predetermined return beam of light from the particular area on the article under test. A sum-frequency camera configured receives a third return beam of light from the particular area on the article under test. Finally, a processor is coupled to control the pulse rate of the infrared light source and the first visible light source and to receive signals from the visible light camera, the visible light second harmonic generation camera, the infrared camera, the infrared second harmonic generation camera and the sum-frequency camera. The processor is configured to process the received signals to determine when the chemical substance applied to the outer surface of the article under test has been absorbed or has cured.

In one further embodiment, a second visible light source controllably outputs a second pulsed beam of coherent visible light. The second visible light source may be configured to direct the second pulsed beam of coherent visible light at the same particular area on the article under test. Also, a third-order camera may be configured to receive a fourth return beam of light from the particular area on the article under test. Finally, the processor may be configured to receive signals from the third-order camera and to process the signals from the third-order camera in addition to the signals from the visible light camera, the visible light second harmonic generation camera, the infrared camera, the infrared second harmonic generation camera and the sum-frequency camera to determine when the chemical substance applied to the outer surface of the article under test has been absorbed or has cured.

In another further embodiment, each of the sources may include an intensity control for setting a predetermined intensity for the respective output beam of light. Also, each of the sources may include a frequency control for setting a predetermined wavelength for the respective output beam of light. Further, each of the sources may include a polarization control for setting a predetermined polarization for the respective output beam of light. Still further, each of the cameras may include an intensity control for setting a predetermined intensity for the respective input beam of light. In addition, each of the cameras may include a frequency control for setting a predetermined wavelength for the respective input beam of light. Each of the cameras may include a polarization control for setting a predetermined polarization for the respective input beam of light. The system may also include a beam splitter configured to split a return beam of light into two portions, a first portion directed to the visible light camera and a second portion directed to the visible light second harmonic generation camera.

In a second aspect, an active real-time characterization system monitors the absorption and/or curing rate of a chemical substance applied to an outer surface of an article under test. An infrared light source is provided for controllably outputting a pulsed beam of coherent infrared light. The infrared light source is configured to direct the pulsed beam of coherent infrared light at a particular area on the article under test where the chemical substance has been applied. A first visible light source is provided for controllably outputting a first pulsed beam of coherent visible light. The first visible light source is configured to direct the first pulsed beam of coherent visible light at the same particular area on the article under test. A visible light camera and a visible light second harmonic generation camera are each configured to receive a first predetermined return beam of light from the same particular area on the article under test. An infrared camera and an infrared second harmonic generation camera are each configured to receive a second predetermined return beam of light from the same particular area on the article under test. Finally, a processor is coupled to control the pulse rate of the infrared light source and the first visible light source and to receive signals from the visible light camera, the visible light second harmonic generation camera, the infrared camera, and the infrared second harmonic generation camera. The processor configured to process the received signals to determine when the chemical substance applied to the outer surface of the article under test has been absorbed or has cured.

In a third aspect, a method monitors the absorption and/or curing rate of a chemical substance applied to an outer surface of an article under test. Pulsed light beams are generated from an infrared light source and a first visible light source. The pulsed light beams are directed at a particular area on the article under test where the chemical substance has been applied. A visible light camera, a visible light second harmonic generation camera, an infrared camera, an infrared second harmonic generation camera and a sum-frequency camera are each aligned to receive light from the infrared light source and first visible light source reflected from the surface of the article under test. Data is acquired from each of the cameras based on the received light. The acquired data from each of the cameras is processed to determine when there are no further chemical changes taking place thereby signifying that the chemical substance has been absorbed or has cured.

In a further embodiment, a pulsed light beam is generated from a second visible light source. The second visible light source is directed at the particular area on the article under test where the chemical substance has been applied. A third-order camera is aligned to receive light from the first visible light source and the second visible light source reflected from the surface of the article under test. Data is acquired from the third-order camera. The data from the third-order camera and the data from the visible light camera, the visible light second harmonic generation camera, the infrared camera, the infrared second harmonic generation camera and the sum-frequency camera is used in processing the acquired data from each of the cameras to determine when there are no further chemical changes taking place thereby signifying that the chemical substance has been absorbed or has cured.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Figure 1:
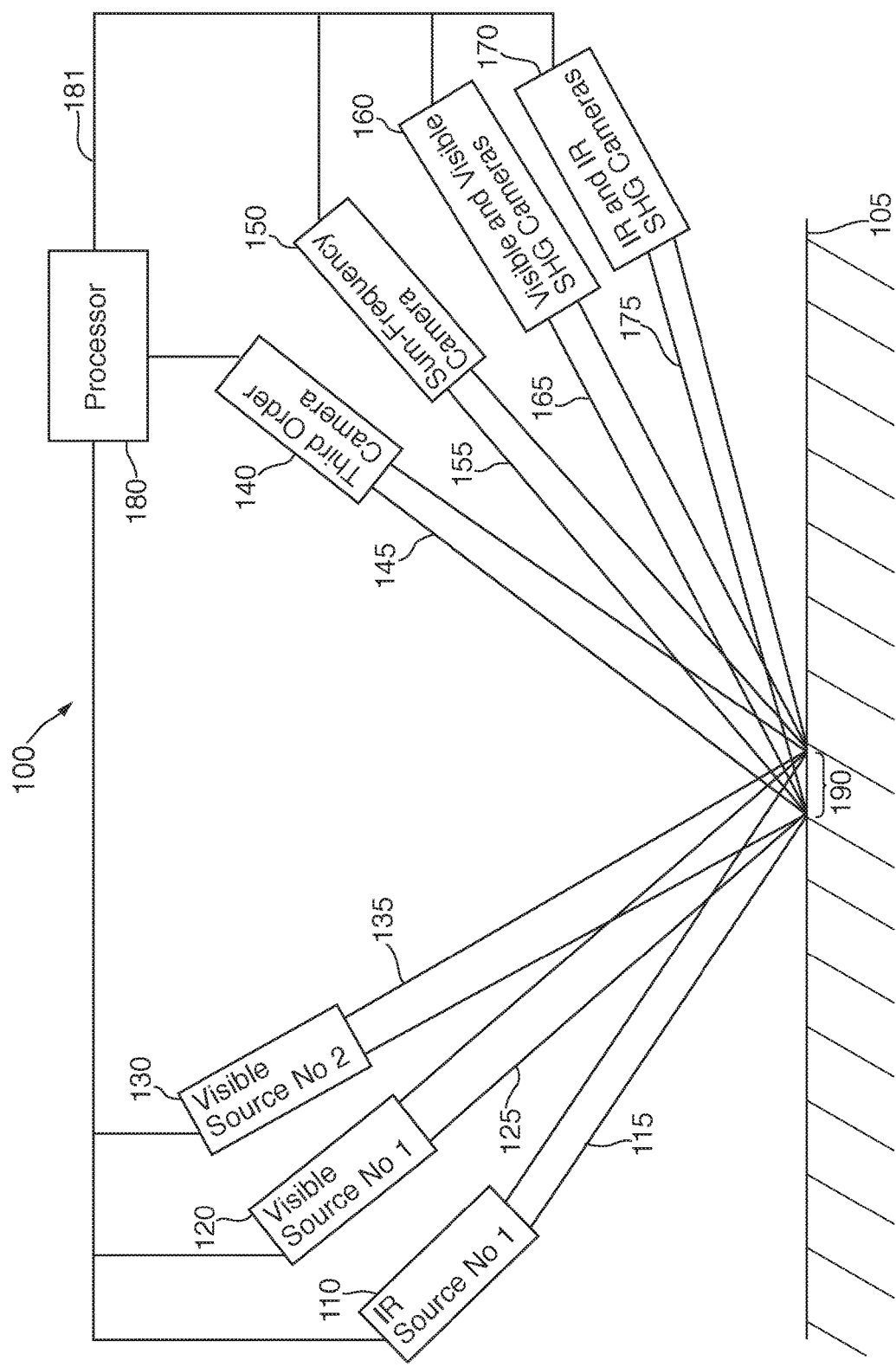
FIG. 1 is a block diagram of an active real-time characterization system for use in monitoring the absorption and curing rate of a chemical substance applied to a part according to an aspect of the present disclosure.

Referring now to FIG. 1, the active real-time characterization system 100 of the present disclosure includes an infrared (IR) light source 110, a first visible light source 120 and a second visible light source 130. Each of the light sources 110, 120, 130 is positioned to controllably direct a pulsed beam of coherent light at an area 190 on a surface 105 of an article under test, e.g., a part having a chemical substance such as a coating, paint, primer, or the like applied to the upper (exposed) surface thereof. In particular, infrared (IR) source 110 is positioned to controllably direct a pulsed beam of coherent light 115 at area 190, first visible light source 120 is positioned to controllably direct a pulsed beam 125 of coherent light at area 190, and second visible light source 130 is positioned to controllably direct a pulsed beam 135 of coherent light at area 190. The pulsed beams 115, 125, 135 may be emitted directly from the respective light sources 110, 120, 130 or may be emitted via respective optical fibers (and appropriate lenses, etc.) coupled to the light sources 110, 120, 130. When beams 115, 125, 135 are emitted via respective optical fibers, each light source 110, 120 130 consists of a laser of the appropriate type (visible or IR light) that is coupled to an input of an associated optical fiber via input optics. The laser is preferably a solid state laser or a diode laser and may be, for example, a pulsed diode laser, a continuous-wave diode laser, a pulsed solid state laser, a continuous-wave solid state laser, a flash-lamp pumped solid state laser, or a diode pumped solid state laser. The input optics consist of an input polarizer, an input wavelength discriminator, an input spatial filter and an input propagation optics. The input polarizer is, for example, a Brewster angle polarizer, a thin film polarizer, a Glan-air or Glan-Thompson polarizer or other crystal polarizer. The wavelength discriminator is, for example, a color filter, a dielectric film, a holographic transmission filter, or a grating. The input propagation optics is formed of one or more refractive or reflective optics which, when used in combination, control the divergence or convergence of the beam as it propagates towards the first input optical fiber. The input optics are optimized for the wavelength of the associated optical source. Coupling optics are coupled to an output of each optical fiber to direct the beam to area 190. IR light source 110 is configured to output light at a fixed, predetermined IR wavelength, while first visible light source 120 is configured to output light at a first fixed, predetermined visible wavelength and second visible light source 130 is configured to output light at a second fixed, predetermined visible wavelength, different from the first fixed, predetermined visible wavelength.

Figure 2:
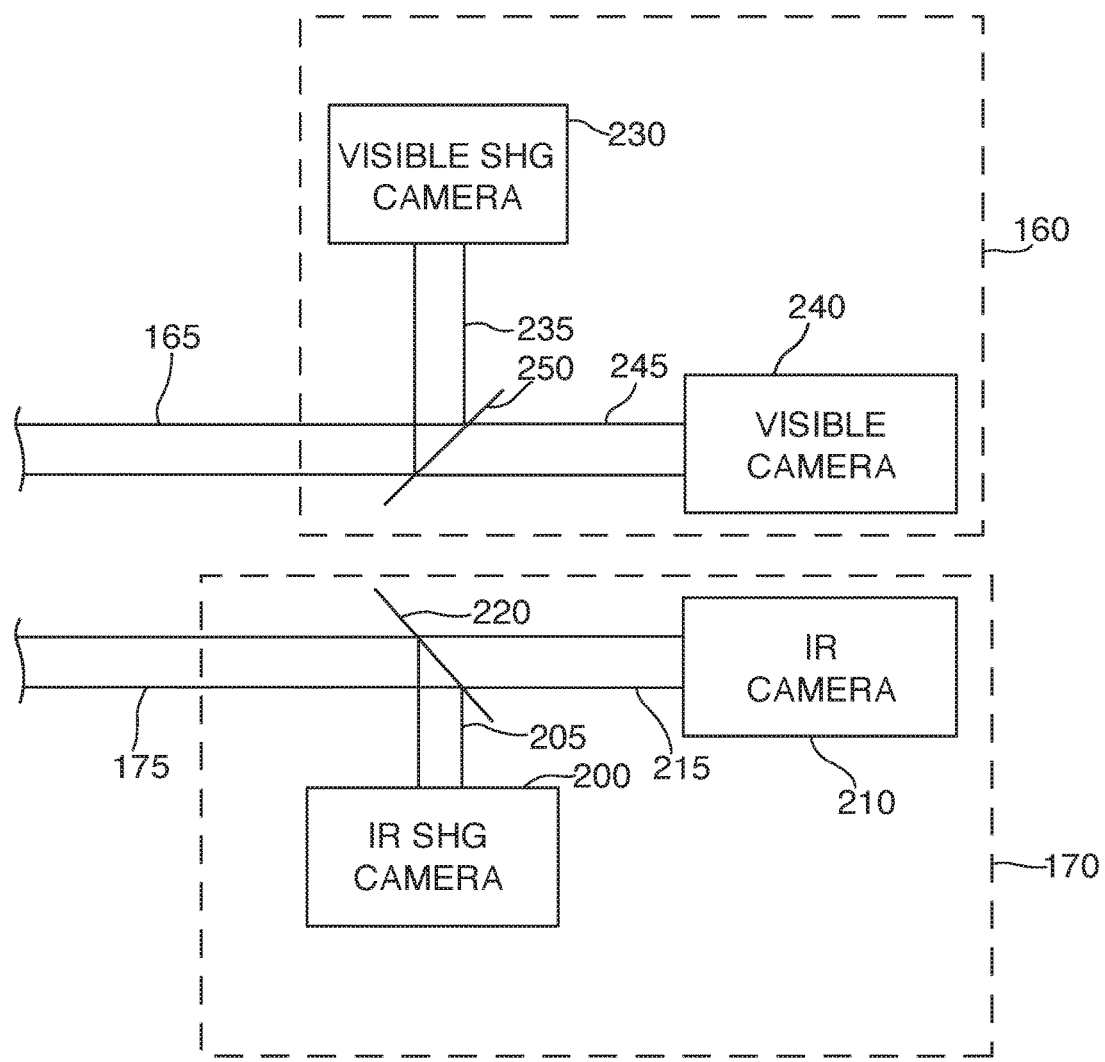
FIG. 2 is a block diagram showing the composition of the infrared light and visible light camera systems according to an aspect of the present disclosure.

System 100 in FIG. 1 also includes a number of cameras for detecting light reflected from the surface 105 of article under test, including a Raman (third-order) camera 140 which receives a light beam 145 and a sum-frequency camera 150 which receives a light beam 155. System 100 also includes paired visible and visible second harmonic generation (SHG) cameras 160 which receive a light beam 165, and paired IR and IR SHG cameras 170 which receive a light beam 175. Referring now to FIG. 2, the paired visible light and visible light second harmonic generation (SHG) cameras 160 include a visible light SHG camera 230 and a visible light camera 240 which are positioned to each receive light beam 165 via a beam splitter 250. In particular, beam splitter 250 is positioned to split light beam 165 into a first portion 235 that is provided to visible light SHG camera 230 and a second portion 245 that is provided to visible light camera 240. Similarly, the paired IR and IR second harmonic generation (SHG) cameras 170 include an IR SHG camera 200 and an IR camera 210 which are positioned to each receive light beam 175 via a beam splitter 220. In particular, beam splitter 220 is positioned to split light beam 175 into a first portion 205 that is provided to IR SHG camera 200 and a second portion 215 that is provided to IR camera 210. Each of the cameras 140, 150, 200, 210, 230 and 240 produces an output signal that is communicated in a conventional manner to a processor 180 in FIG. 1 via a link 181 for processing as discussed below. As also discussed below, the reflected light beams 145, 155, 165 and 175 are at a particular angle with respect to the surface 105 of article under test based on the fixed angles that light beams 115, 125 and 135 are directed at the surface 105 of article under test. The cameras 140, 150, 200, 210, 230 and 240 are thus positioned to receive such light beams. Each camera 140, 150, 200, 210, 230, 240 is a conventional detector as defined below with respect to FIG. 4.

As one of ordinary skill in the art will readily recognize, light sources 110, 120, 130 and cameras 140, 150, 200, 210, 230 and 240 may be fixed in place and the article under test may be moved so that the area 190 of the light beams 115, 125, 135 moves over the entire surface 105 of the article under test. In another embodiment, light sources 110, 120, 130 and cameras 140, 150, 200, 210, 230 and 240 may be mounted on a fixture that moves along the surface 105 of the article under test. In yet another embodiment, light sources 110, 120, 130 may be arranged to raster the respective output light beams 115, 125, 135 across the surface 105 of the article under test, and the cameras 140, 150, 200, 210, 230 and 240 arranged to move proportionally to receive the respective associated return light beams 145, 155, 165, 175.

Figure 3:
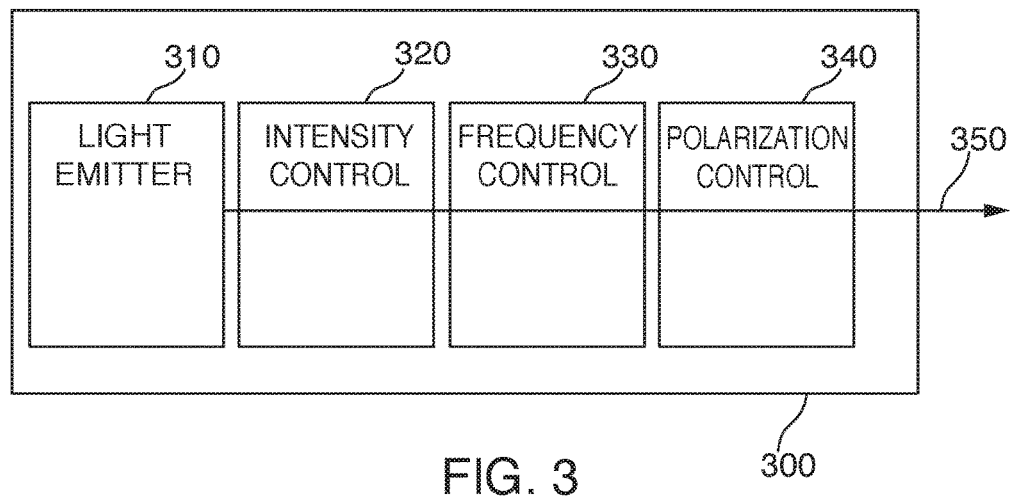
FIG. 3 is a block diagram showing the composition of the light sources according to an aspect of the present disclosure.

Referring now to FIG. 3, each of the light sources 110, 120, 130 is configured similarly, as shown by representative light source 300, but each may be configured for a different intensity, frequency and/or polarization. Light source 300 includes a light emitter 310, an intensity control 320, a frequency control 330 and a polarization control 340 for outputting a light beam 350. Light emitter 310 is preferably a narrow frequency bandwidth visible pulse laser and, may be, for example a pulsed diode laser, a continuous wave diode laser or a pulsed solid state laser or a continuous wave solid state laser. Intensity controls may include broadband filters for reducing intensity or may specifically refer to certain frequency notch filters which are intended to drop intensity levels where the cameras can act in a linear fashion. Frequency controls can be accomplished in simple cases by frequency dependent color filters or notch filters and in more elaborate by a spectrophotometer that is typically composed of a diffraction grating which operates at a frequency or bandwidth of interest. The key point for the frequency control is to ensure that only light in beam 350 is directed at the surface 105 and that stray light produced by light emitter 310 is removed, and as one of ordinary skill in the art will readily recognize, other frequency selective elements may also be used. Polarization control 340 typically consists of two separate optical elements, a polarizer which only passes light of one polarization and a polarization modifying element—typically a halfway plate or a quarter wave plate. A halfway plate is used to rotate the polarization to the desired orientation. A quarter wave plate is used to change the polarization from linear to circular or from circular to linear as needed. As shown, the polarizer is the last element before light beam 350 leaves the source and heads for the surface 105. Each light source 110, 120, 130 is configured, based on the selection of light emitter 310, intensity control 320, frequency control 330 and polarization control 340 in each to provide a respective beam 115, 125, 135 of coherent light.

Figure 4:
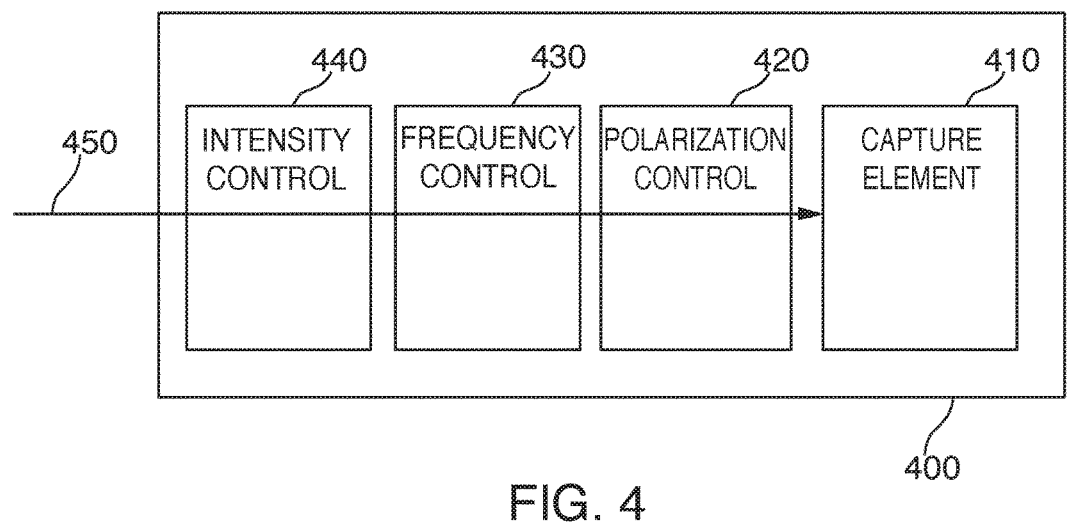
FIG. 4 is a block diagram showing the composition of the cameras according to an aspect of the present disclosure.

Referring now to FIG. 4, each of the cameras 140, 150, 200, 210, 230 and 240 is configured similarly, as shown by representative camera 400. Camera 400 includes a capture element 410, a polarization control 420, a frequency control 430 and an intensity control 440 for receiving light beam 450. Exemplary capture elements 34 include, without limitation, cameras, charge-coupled devices, imaging arrays, photometers, and like devices. The frequency control 430 and intensity control 440 operate on light beam 450 in a similar manner as intensity control 320 and frequency control 330 operate on light beam 350 as discussed above. Preferably, polarization control 420 consists of a half wave plate and quarter wave combination, followed by a polarizer.

In operation, the system 100 shown in FIG. 1 provides a combination of linear infrared spectroscopy, second order surface frequency mixing spectroscopy, and third-order non-linear optics (e.g., Raman spectroscopy) spectroscopy. System 100 provides a number of ways of performing species identification and allows the cross correlation between the three types of spectroscopies in order to avoid false negative spectral features.

In particular, visible light source 120 and IR light source 110 are configured and positioned to provide light signals which allow the processor 180 to generate simultaneous linear (same frequency) and non-linear (second harmonic generation) real time spectroscopic signals, in conjunction with paired visible light and visible light second harmonic generation (SHG) cameras 160 and paired IR and IR SHG cameras 170. As one of ordinary skill in the art will readily recognize, paired visible light and visible light second harmonic generation (SHG) cameras 160 and paired IR and IR SHG cameras 170 are positioned at a particular predetermined angle to receive the appropriate respective return light beams 165, 175 from surface 105.

Further, visible light source 120 and IR light source 110 are also configured and positioned to provide light signals which allow the processor 180 to generate a sum-frequency ($\omega_{IR}+\omega_{VISIBLE}$) real-time spectroscopic signal, in conjunction with sum-frequency camera 150. As one of ordinary skill in the art will readily recognize, sum-frequency camera 140 is positioned at a particular predetermined angle to receive the appropriate return light beams 155 from surface 105.

Finally, visible light source 120 and visible light source 130 are configured and positioned to provide light signals which allow the processor 180 to generate a third-order ($2\omega_{VIS1}-\omega_{VIS2}$) (e.g., Raman) real-time spectroscopic signal, in conjunction with Raman (third-order) camera 140. As one of ordinary skill in the art will readily recognize, Raman (third-order) camera 140 is positioned at a particular predetermined angle to receive the appropriate return light beams 145 from surface 105.

Processor 180 is coupled to each light source, i.e., IR light source 110 and visible light sources 120, 130, via a link 182 to control the pulse rate thereof. The pulse rate is determined based on a number of factors, including hardware limitations and environmental concerns. Ideally, the pulse rate of each light source is set as high as possible to allow for the fastest data collection. However, the pulse rate for an actual implementation is limited by cost and/or implementation difficulty in the hardware. In addition, higher pulse rates may, in some cases, be so fast that their presence could alter the chemical processes occurring at the surface (e.g., by heating the surface). Thus the pulse rate must be kept below a threshold whereby physical properties at the surface are not altered by the pulsed light provided by the light sources. This is done by limiting both the peak power and the average power of the light beams provided by each light source. Processor 180 is coupled to receive signals from each of cameras 140, 150, 200, 210, 230 and 240 and is configured to calculate in real time a linear spectroscopic signal, a second harmonic generation spectroscopic signal, a sum-frequency spectroscopic signal and a third-order spectroscopic signal. The processor 180 is also configured to compare each calculated signal with each other calculated signal and with a predetermined baseline signal to ensure that the article under test conforms to an expected value. When the processor 180 determines that the calculated signals indicate that the article under test does not conform to the expected value, processor 180 provides a fault signal which may be used to halt formation of the article under test for either repair thereof or so that the article under test may be immediately discarded.

Figure 5:
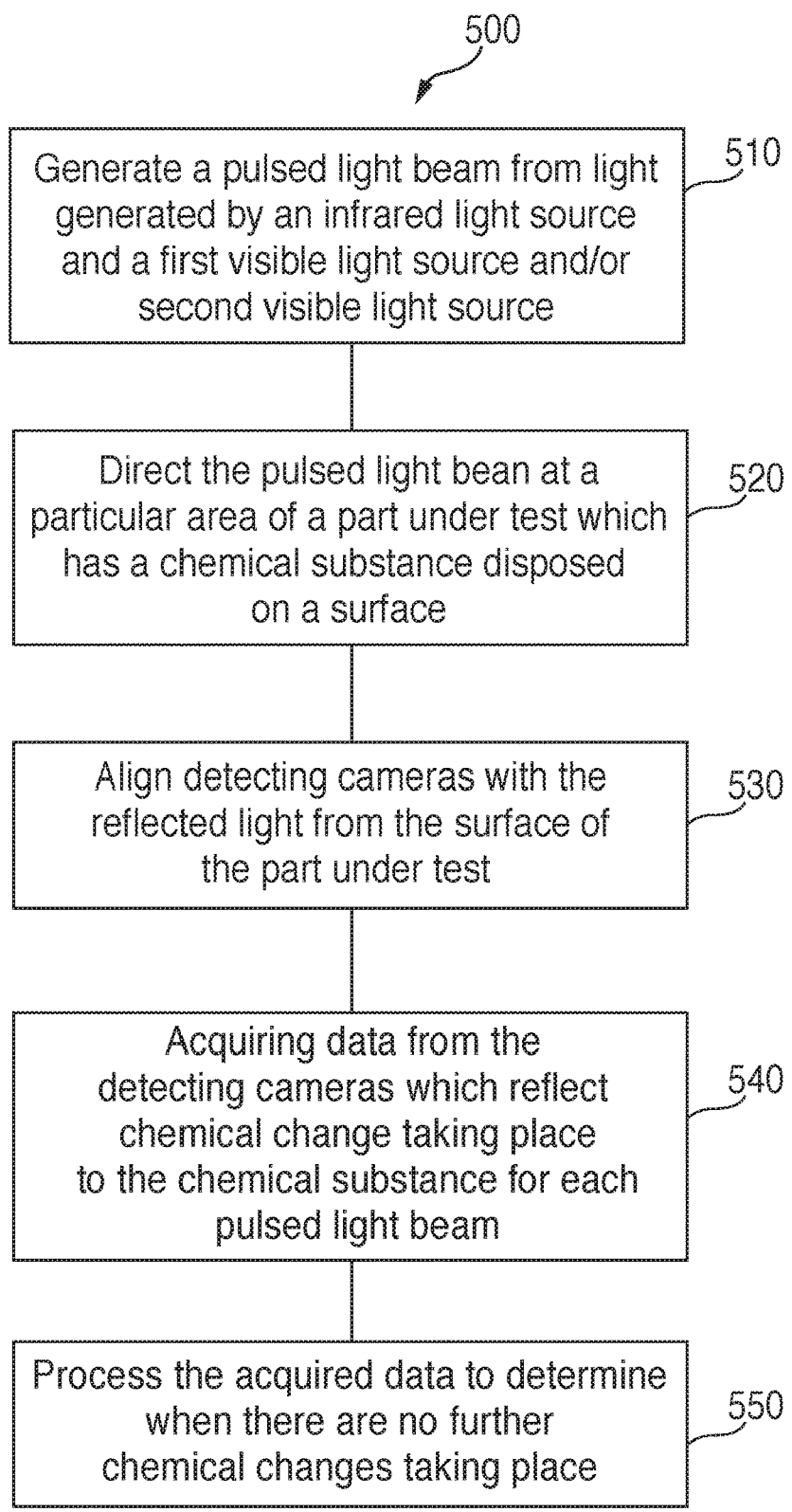
FIG. 5 is a flow chart of a method for operating the active real-time characterization system of the present disclosure.

Referring now to FIG. 5, a flow chart 500 of a method for operating the active real-time characterization system of the present disclosure is shown. In step 510, a pulsed light beam is generated by an infrared light source, a first visible light source, and/or a second visible light source. Next, at step 520, the pulsed light beam is directed at a particular area of a part under test which has a chemical substance disposed on an exposed upper surface thereof. Thereafter, at step 530, detecting cameras are aligned to receive the reflected light from the surface of the part under test. Next, at step 540, data is acquired from the detecting cameras which reflects any chemical change taking place to the chemical substance for each pulsed light beam. Thereafter, at step 550, the acquired data is processed to determine when there are no further chemical changes taking place. The lack of chemical changes signifies, for example, that the particular chemical has been absorbed or cured without requiring any contact whatsoever with the part under test.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. An active real-time characterization system for monitoring the absorption and/or curing rate of a chemical substance applied to an outer surface of an article under test, comprising:
   an infrared light source for controllably outputting a pulsed beam of coherent infrared light, the infrared light source configured to direct the pulsed beam of coherent infrared light at a particular area on the article under test where the chemical substance has been applied;
   a first visible light source for controllably outputting a first pulsed beam of coherent visible light, the first visible light source configured to direct the first pulsed beam of coherent visible light at the same particular area on the article under test;
   a visible light camera and a visible light second harmonic generation camera, the visible light camera and visible light second harmonic generation camera each configured to receive a first predetermined return beam of light from the particular area on the article under test;
   an infrared camera and an infrared second harmonic generation camera, the infrared camera and infrared second harmonic generation camera each configured to receive a second predetermined return beam of light from the particular area on the article under test;
   a sum-frequency camera configured to receive a third return beam of light from the particular area on the article under test; and
   a processor coupled to control a pulse rate of the infrared light source and the first visible light source and to receive signals from the visible light camera, the visible light second harmonic generation camera, the infrared camera, the infrared second harmonic generation camera and the sum-frequency camera, the processor configured to process the received signals to determine when the chemical substance applied to the outer surface of the article under test has been absorbed or has cured.

2. The active real-time characterization system of claim 1, further comprising:
   a second visible light source for controllably outputting a second pulsed beam of coherent visible light, the second visible light source configured to direct the second pulsed beam of coherent visible light at the same particular area on the article under test;
   a third-order camera configured to receive a fourth return beam of light from the particular area on the article under test; and
   wherein the processor is configured to receive signals from the third-order camera and to process the signals from the third-order camera in addition to the signals from the visible light camera, the visible light second harmonic generation camera, the infrared camera, the infrared second harmonic generation camera and the sum-frequency camera to determine when the chemical substance applied to the outer surface of the article under test has been absorbed or has cured.

3. The active real-time characterization system of claim 1, wherein each of the light sources includes an intensity control for setting a predetermined intensity for a respective output beam of coherent light.

4. The active real-time characterization system of claim 1, wherein each of the light sources includes a frequency control for setting a predetermined wavelength for a respective output beam of coherent light.

5. The active real-time characterization system of claim 1, wherein each of the light sources includes a polarization control for setting a predetermined polarization for a respective output beam of coherent light.

6. The active real-time characterization system of claim 1, wherein each of the cameras includes an intensity control for setting a predetermined intensity for a respective input beam of light.

7. The active real-time characterization system of claim 1, wherein each of the cameras includes a frequency control for setting a predetermined wavelength for a respective input beam of light.

8. The active real-time characterization system of claim 1, wherein each of the cameras includes a polarization control for setting a predetermined polarization for a respective input beam of light.

9. The active real-time characterization system of claim 1, further comprising a beam splitter configured to split a return beam of light into two portions, a first portion directed to the visible light camera and a second portion directed to the visible light second harmonic generation camera.

10. An active real-time characterization system for monitoring the absorption and/or curing rate of a chemical substance applied to an outer surface of an article under test, comprising:
   an infrared light source for controllably outputting a pulsed beam of coherent infrared light, the infrared light source configured to direct the pulsed beam of coherent infrared light at a particular area on the article under test where the chemical substance has been applied;
   a first visible light source for controllably outputting a first pulsed beam of coherent visible light, the first visible light source configured to direct the first pulsed beam of coherent visible light at the same particular area on the article under test;

a visible light camera and a visible light second harmonic generation camera, the visible light camera and visible light second harmonic generation camera each configured to receive a first predetermined return beam of light from the same particular area on the article under test;

an infrared camera and an infrared second harmonic generation camera, the infrared camera and infrared second harmonic generation camera each configured to receive a second predetermined return beam of light from the same particular area on the article under test; and a processor coupled to control a pulse rate of the infrared light source and the first visible light source and to receive signals from the visible light camera, the visible light second harmonic generation camera, the infrared camera, and the infrared second harmonic generation camera, the processor configured to process the received signals to determine when the chemical substance applied to the outer surface of the article under test has been absorbed or has cured.

11. The active real-time characterization system of claim 10, further comprising:

a second visible light source for controllably outputting a second pulsed beam of coherent visible light, the second visible light source configured to direct the second pulsed beam of coherent visible light at the same particular area on the article under test;

a sum-frequency camera configured to receive a fourth return beam of light from the particular area on the article under test; and wherein the processor is configured to receive signals from the sum-frequency camera and to process the signals from the sum-frequency camera in addition to the signals from the visible light camera, the visible light second harmonic generation camera, the infrared camera, and the infrared second harmonic generation camera to determine when the chemical substance applied to the outer surface of the article under test has been absorbed or has cured.

12. The active real-time characterization system of claim 10, wherein each of the light sources includes an intensity control for setting a predetermined intensity for a respective output beam of coherent light.

13. The active real-time characterization system of claim 10, wherein each of the light sources includes a frequency control for setting a predetermined wavelength for a respective output beam of coherent light.

14. The active real-time characterization system of claim 10, wherein each of the light sources includes a polarization control for setting a predetermined polarization for a respective output beam of coherent light.

15. The active real-time characterization system of claim 10, wherein each of the cameras includes an intensity control for setting a predetermined intensity for a respective input beam of light.

16. The active real-time characterization system of claim 10, wherein each of the cameras includes a frequency control for setting a predetermined wavelength for a respective input beam of light.

17. The active real-time characterization system of claim 10, wherein each of the cameras includes a polarization control for setting a predetermined polarization for a respective input beam of light.

18. The active real-time characterization system of claim 10, further comprising a beam splitter configured to split a return beam of light into two portions, a first portion directed to the visible light camera and a second portion directed to the visible light second harmonic generation camera.

19. A method for monitoring the absorption and/or curing rate of a chemical substance applied to an outer surface of an article under test, comprising the steps of:

generating pulsed light beams from an infrared light source and a first visible light source;

directing the pulsed light beams at a particular area on the article under test where the chemical substance has been applied;

aligning a visible light camera, a visible light second harmonic generation camera, an infrared camera, an infrared second harmonic generation camera and a sum-frequency camera to receive light from the infrared light source and first visible light source reflected from the outer surface of the article under test;

acquiring data from each of the cameras based on the received light; and processing the acquired data from each of the cameras to determine when there are no further chemical changes taking place thereby signifying that the chemical substance has been absorbed or has cured.

20. The method of claim 19, further comprising the steps of:

generating a pulsed light beam from a second visible light source;

directing the second visible light source at the particular area on the article under test where the chemical substance has been applied;

aligning a third-order camera to receive light from the first visible light source and the second visible light source reflected from the outer surface of the article under test;

acquiring data from the third-order camera; and using the data from the third-order camera and the data from the visible light camera, the visible light second harmonic generation camera, the infrared camera, the infrared second harmonic generation camera and the sum-frequency camera in processing the acquired data from each of the cameras to determine when there are no further chemical changes taking place thereby signifying that the chemical substance has been absorbed or has cured.

* * * * *